United States Patent [19]

Stanton

[11] 4,392,496

[45] Jul. 12, 1983

[54] NEUROMUSCULAR STIMULATOR

[75] Inventor: David J. Stanton, Anoka, Minn.

[73] Assignee: Medtronic, Inc., Minneapolis, Minn.

[21] Appl. No.: 243,558

[22] Filed: Mar. 13, 1981

[51] Int. Cl.³ .............................................. A61N 1/36
[52] U.S. Cl. ................................................ 128/423 W
[58] Field of Search ......................... 128/421, 422, 423

[56] References Cited

U.S. PATENT DOCUMENTS

| | | | |
|---|---|---|---|
| 3,344,792 | 1/1965 | Offner et al. | 128/419 |
| 3,478,744 | 11/1969 | Leiter | 128/423 R |
| 3,794,022 | 2/1974 | Nawracaj et al. | 128/422 |
| 3,888,261 | 6/1975 | Maurer | 128/421 |
| 3,983,881 | 10/1976 | Wickham | 128/422 |

Primary Examiner—William E. Kamm
Attorney, Agent, or Firm—Schroeder, Siegfried, Vidas, Steffey & Arrett

[57] ABSTRACT

A dual channel neuromuscular stimulator. Pulses developed by a pulse generator are transmitted alternately on both channels to involuntarily contract muscles. The stimulator has variable on/off cycling capability to provide flexibility in meeting the stimulation needs of patients and has output current adjustments and other variable parameter settings to achieve optimum neuromuscular stimulation. To enhance patient comfort, the stimulation output of the stimulator can be slowly "ramped up" to its full stimulation power to allow the increase in stimulation to occur at various rates to accommodate the differing characteristics of different muscle groups. A jack is provided to permit the stimulation to be controlled by an external switch operated by a clinician to coordinate stimulation of various muscle groups with voluntary muscle contraction by the patient. The jack can also be connected to a heel operated switch to stimulate muscle groups to allow certain disabled persons to walk normally. The balanced biphasic output waveform of the stimulator has a zero net DC component to minimize the possibility of skin rash developing from stimulation.

12 Claims, 5 Drawing Figures

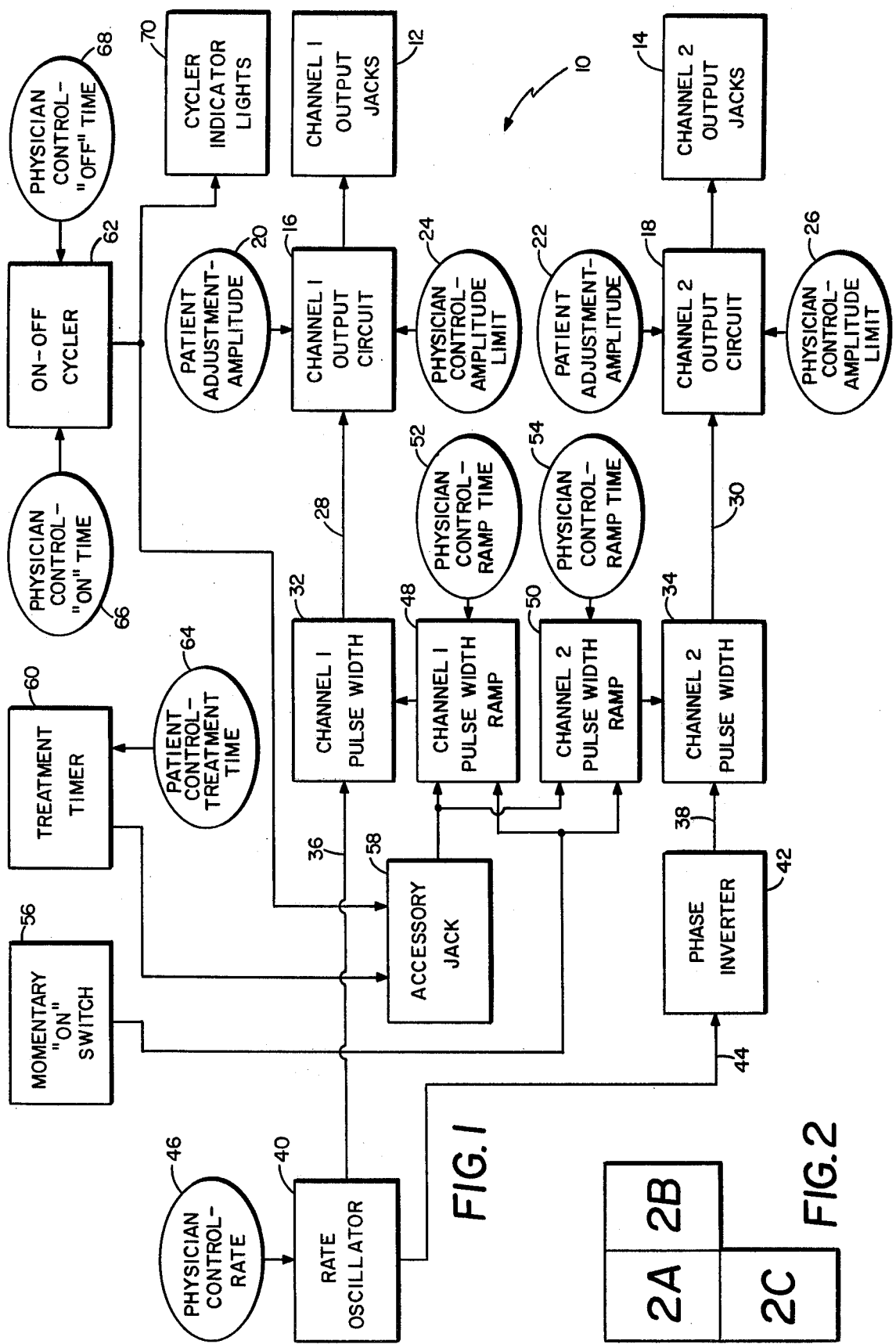

NEUROMUSCULAR STIMULATOR

BACKGROUND OF THE INVENTION

Electrical stimulation of various biological systems is known in the prior art. For example, pain alleviation through nerve stimulation or motor control through nerve or muscle stimulation have been successfully demonstrated.

One of the uses for neuromuscular stimulator systems is to provide muscle stimulation to assist partially disabled stroke victims in raising the toe to the affected leg during that portion of the walking motion where the foot and heel are off the ground. Systems for accomplishing such stimulation under the control of a heel switch are shown, for example, in Offner et al U.S. Pat. No. 3,344,792.

An implantable system to correct for foot drop is discussed in "Developing Clinical Devices for Hemiplegic Stroke Patients (Revised)" by Edward Schuck, Harry Friedman and others in a paper originally presented at the Fourth International Symposium on External Control of Human Extremities, Aug. 28–Sept. 2, 1972, at Dubrovnik, Yugoslavia.

The improved neuromuscular stimulator of the present invention provides a stimulator with dual channel capabilities for simultaneous neuromuscular stimulation at two sites to provide a more comprehensive treatment device to reduce the amount of time needed to administer a stimulation treatment program. The variable on/off cycling capability allows the user to select stimulation parameters effective for exercising muscles to prevent disuse atrophy while minimizing muscle fatigue. The optional control of the device through a remote switch connected to an "accessory" jack allows for more flexible application of the stimulator to treatment of varying conditions.

SUMMARY OF THE INVENTION

Briefly described, the apparatus of this invention and its preferred embodiment comprise a portable neuromuscular stimulation system for use to provide external electrical stimulus induced muscle exercise to retard or prevent disuse atrophy and for other purposes such as the correction of hemiplegic foot drop. The stimulator provides, on two output channels, alternating pulsed stimulation signals which are connected to electrodes through flexible cables. The pulsed signals, when applied, are increased in intensity at a variable rate until a fixed intensity is reached. The pulses are applied during an adjustable predetermined stimulation interval and removed for an adjustable predetermined resting interval which occurs alternately during a particular treatment interval which is preset by a treatment timer time selector. The amplitude limit of the pulse at the output channels is individually adjustable by the patient within an upper limit which is independently established by a clinician for each channel at the time the device is set up for the patient.

The time delay required for the increase of output pulses to their full selected power may be independently adjusted for each channel by clinician controls. The pulse rate of the stimulation pulses may also be established by a clinician control. A patient accessible control provides a constant train of stimulation pulses when actuated and an accessory input jack allows the control of pulse trains from either an external physician controlled switch or from a heel switch when the stimulator is used to correct hemiplegic foot drop.

BRIEF DESCRIPTION OF THE DRAWINGS

FIG. 1 is a simplified functional block diagram of the dual channel neuromuscular stimulator system, according to the present invention.

DETAILED DESCRIPTION OF THE PREFERRED EMBODIMENT

Figure 2A:
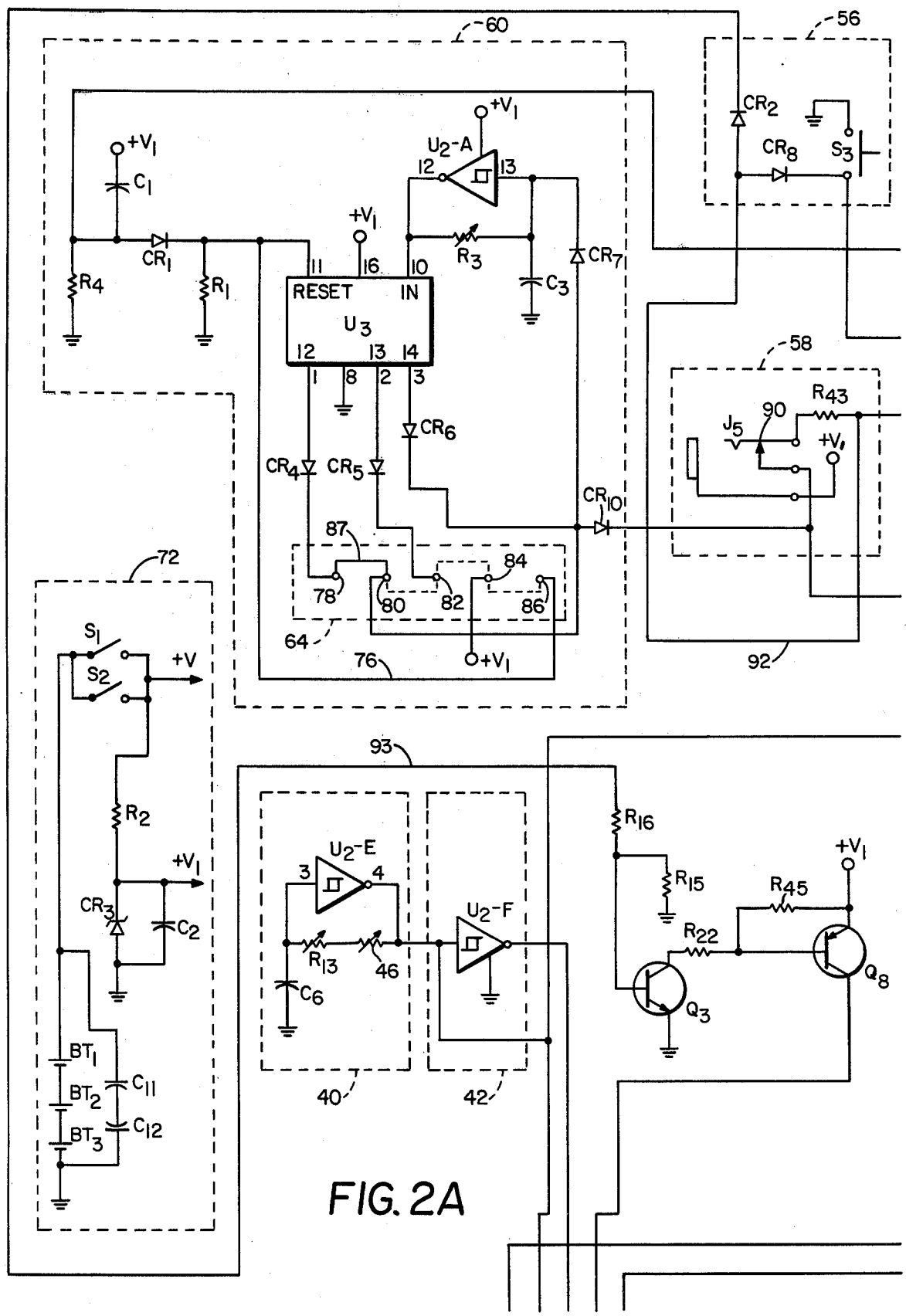
FIG. 2 is a layout of the detailed schematic of FIGS. 2A through 2C which show the circuitry of the neuromuscular stimulation system.

Referring first to FIG. 1, there is shown a simplified block diagram of the dual channel neuromuscular stimulator system of the present invention. The overall unit 10 has a pair of output jacks 12 and 14 which can be connected to suitable stimulation electrodes, such as Medtronic Conductive Carbon Electrodes #3791, 3793, 3794 or 3795, through normal plug-in cables such as Medtronic #3781 cable. The electrodes are affixed to the skin over the muscle and nerve tissue to be stimulated using Neuromod ® TENS electrode gel and tape patches for the selected carbon electrode.

The circuitry providing the exitation at output jacks 12 and 14 is identical for channels 1 and 2. Each channel has a constant current output circuit 16 and 18. Individual patient adjusted amplitude controls 20 and 22 provide an adjustment of stimulation pulse amplitude which is accessible to the patient. Additionally, a physician or clinician controlled amplitude limit adjustment 24 and 26 is also provided for each channel. The clinician controls are located under a protective cover in the device to limit their accessibility to the patient. The physician accessible limit controls 24 and 26 allow the physician to establish an upper limit for stimulation amplitude as well as allowing the patient adjusted amplitude controls 20 and 22 to be adjustable over the most desirable part of the range of operating amplitudes.

The drive signals 28 and 30 to the output circuits 16 and 18 are provided by identical channel 1 and channel 2 pulse width circuits 32 and 34. The pulse width circuits are driven by input signals 36 and 38 which are supplied respectively by a rate oscillator 40 and a phase inverter 42 which receives its input signal 44 from rate oscillator 40. Rate oscillator 40 has a physician controlled adjustment means 46 to alter the oscillation rate. In the preferred embodiment shown, the pulse rate is adjustable between 3 and 50 pulses per second.

Additional inputs to the pulse width circuits 32 and 34 are provided by pulse width ramp generation circuits 48 and 50. The ramp circuits 48 and 50 are adjustable by clinician controlled ramp time adjustment means 52 and 54, respectively. The pulse width ramp circuits 48 and 50 also receive inputs from a momentary "on" switch 56 which is also referred to herein as a "constant stimulation" actuating switch. Further inputs to the pulse width ramp circuits 48 and 50 are provided through accessory jack 58. The accessory jack may be connected to an external switch such as a physician controlled switch which may be used during calibration of the stimulator to apply pulses independent of the status of separate "on" and "off" time controls discussed below. Signals controlling the pulse width ramp circuits from the treatment timer 60 and on/off cycler 62 are also passed through the accessory jack 58 as shown more fully in the detailed schematic of FIGS. 2A through 2C.

Treatment timer 60 receives an input from a patient control 64 to set the length of the treatment time and shut down the operation of the stimulator after the selected treatment time has elapsed. The on/off cycler 62 provides for intermittent operation of the circuitry during a treatment to apply pulses in bursts having a predetermined time duration and to suppress the pulse output during a predetermined "off" time or rest interval as established by physician actuated adjustment controls 66 and 68. The treatment timer provides for treatment time of 15, 30 or 60 minutes or continuous operation while the on/off cycler provides alternative stimulation and resting intervals of 2 to 25 seconds and 2 to 50 seconds, respectively.

Figure 2B:
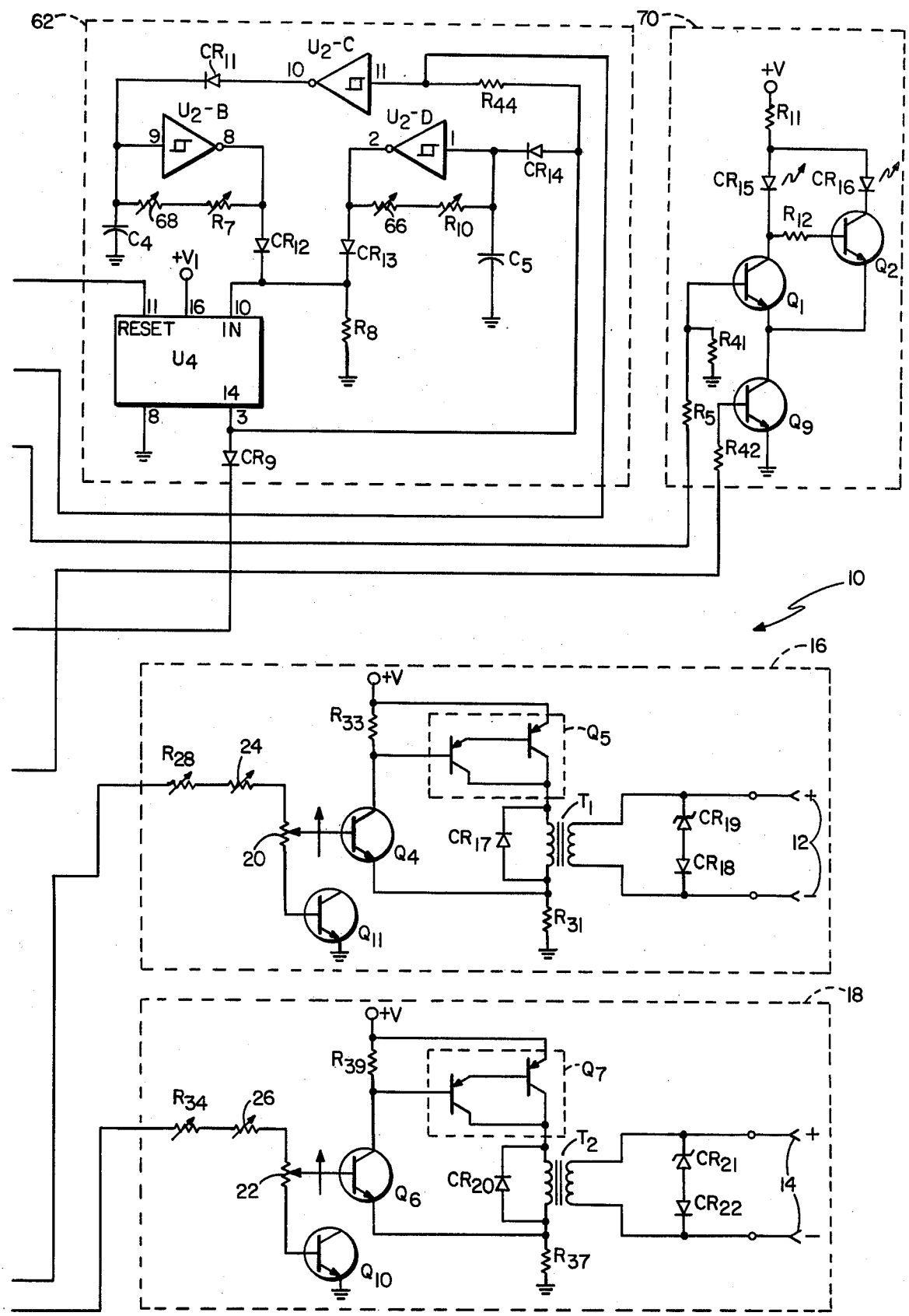
Figure 2C:
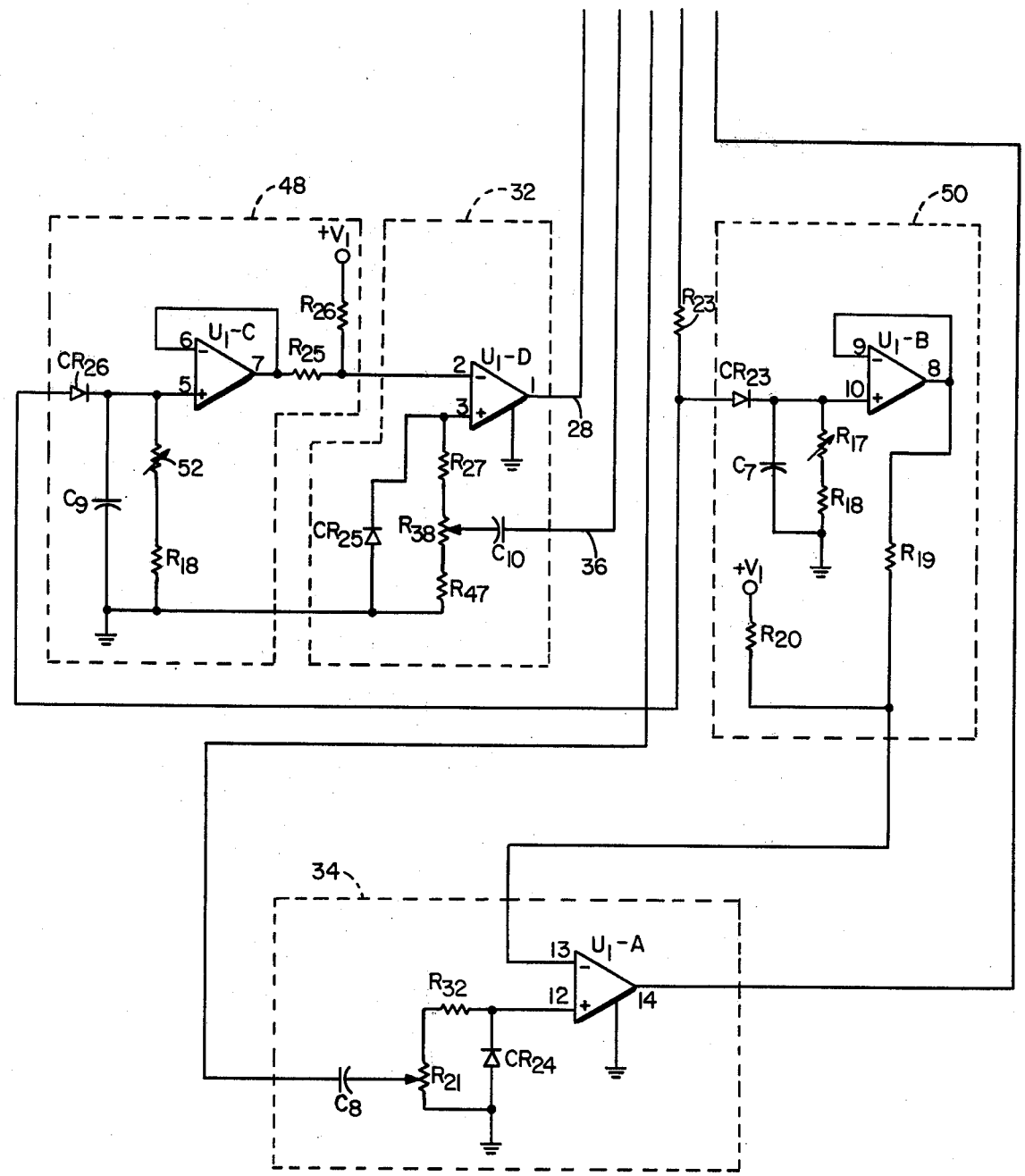

Referring now to FIGS. 2A through 2C, there is shown a detailed schematic diagram of the dual channel neuromuscular stimulator system according to the present invention. The broken line boxes in FIGS. 2A through 2C correspond generally to the similarly numbered boxes in the functional block diagram of FIG. 1. Box 72 encloses power source circuitry not explicitly shown in FIG. 1.

The details of construction and operation of the various block elements shown in FIG. 1 and FIGS. 2A through 2C is described below.

The dosage timer 60 utilizes as the principal timing means a 14-stage binary CMOS counter U3 manufactured by Fairchild and others as a model 4020. The numbers at the outside of the box U3 denote the manufacturer's pin designations for the various terminals and the lettering on the inside of the box indicates the functional description of the various U3 terminals utilized in dosage timer 60. The three outputs from the counter U3 at pins 1, 2 and 3 are from the 12th, 13th and 14th counter stages, respectively, and are connected to diodes CR4, CR5 and CR6. The input to U3 at terminal 10 is provided by a Schmitt trigger circuit U2A utilizing one element of a Schmitt trigger module such as a model 40106 unit manufactured by RCA, National Semiconductor and others which contains six Schmitt triggers. The adjustable feedback resistor R3 and timing capacitor C3 operate to establish the frequency of Schmitt trigger U2A as an oscillator to provide a clock signal to the input to U3. In a preferred embodiment of the stimulator, the clock signal is selected to provide outputs at stages 12, 13 and 14 of the binary counter at 15, 30 and 60 minutes, respectively. By selecting the appropriate output from counter U3, it is then possible to obtain a logic signal at either 15, 30 or 60 minutes for use in terminating the treatment.

The treatment timer is reset as the unit is initially powered up by the voltage divider comprised of capacitor C1, diode CR1 and resistor R1. When the "power on" switches S1 and/or S2 are closed, the +V voltage is applied to the various circuits to which it is connected and a regulated V1 voltage is developed across CR3. In the preferred embodiment shown, S1 and S2 are included in the patient amplitude controls 20 and 22, respectively. Capacitor C2 is charged almost instantaneously through limiting resistor R2 and provides a filtering effect for the regulated voltage V1 across CR3. When V1 is applied to C1 as either S1 or S2 is closed to energize the stimulator, C1 begins with no stored voltage so that the charging current passing from V1 to ground through CR1 and R1 develops a positive voltage across R1 to apply a reset signal to terminal 11 of U3. After C1 is fully charged, the charging current drops to zero and thereby removes the reset signal to allow the input clock signal at terminal 10 of U3 to begin the counting operation.

A reset signal can also be applied to the dosage counter U3 by conductor 76 which is connected to terminal 86 of a four-position slide switch 64 which provides the adjustment to select the desired treatment time. Slide switch 64 has terminals 78, 80, 82, 84 and 86. In the first position, the movable conductive element 87 in the slide switch shorts terminals 78 and 80 together; in the second position it shorts terminal 80 to 82; and, in a third position, shorts terminal 82 to 84 and finally, in the fourth position, shorts terminal 84 to terminal 86. In the first position, a 15-minute time interval is selected, in the second, a 30-minute time interval, in the third, a 60-minute time interval and, in the fourth position, because terminal 84 is connected to regulated supply at V1, a positive voltage is connected to the reset input of timer U3 to cause the stimulator to operate in a continuous mode since the treatment timer counter has been disabled by application of constant voltage to its reset terminal. It is particularly convenient to have the continuous operating mode switch position available when the physician is adjusting the various physician controlled parameters of the stimulator to avoid having the stimulator shut off by the treatment timer 60 while adjustments are being made. In the schematic in FIG. 2A, terminals 78 and 80 are shown shorted together, representative of the switch being in position 1 selecting 15-minute operation. The other switch positions for wiper 87 are shown in phantom or dotted line form in FIG. 2A.

When the count in counter U3 reaches the 12th stage of the 14-stage counter, a positive voltage is applied through CR4 to terminal 78, through the switch contact to terminal 80 and through CR7 to the input at terminal 13 to the Schmitt trigger oscillator U2A to stop operation of the oscillator after the desired time has been reached. This is done for the three time intervals of 15, 30 and 60 minutes so that the "end of treatment command" signal will not be erroneously removed by the count advancing to the next stage in the 14-stage binary counter U3.

The output signal from the selected 12th, 13th or 14th stage of the 14-stage binary counter U3 is connected through diode CR10 and normally closed switch contact of accessory jack J5 to the remainder of the circuit where it is used, as described below, to disable the application of stimulation pulses by the circuitry after the desired treatment time has elapsed. The normally closed contact 90 in accessory jack J5 is opened when an accessory switch is used to bypass the treatment timer.

In addition to the treatment timer reset pulse which is generated by C1, CR1 and R1 when the system is powered up, a reset signal can also be applied to the treatment timer counter by switching the selector switch 64 to the fourth position to bridge contacts 84 and 86 and apply the voltage V1 directly to the reset input terminal 11 of the dosage timer. When the switch is set in this position, the stimulation circuit is in continuous operation at the selected pulse rate and at the selected on and off cycle time and the treatment time is not being measured by the counter U3. Of course, the resetting of counter U3 removes any positive output signals from the 12th, 13th and 14th binary stages to allow the Schmitt trigger oscillator U2A to resume operation at the beginning of its timing cycle.

In addition to the treatment timer 60, the circuit 10 includes a cycle timer 62, the details of which are shown in FIG. 2B. The cycle timer 62 establishes the "on" or stimulation and "off" or resting time intervals which alternate during the selected treatment time in accordance with clinician adjustable controls 66 and 68 which are variable resistors appearing in the circuit of the cycle timer 62 as shown in FIG. 2B.

The variable resistor 66 is in the feedback circuit of Schmitt trigger U2D in series with a calibration resistor R10. In order to have Schmitt trigger U2D operate as an oscillator, a capacitor C5 is connected from its input terminal 1 to ground. The output of the Schmitt trigger oscillator U2D is passed through diode CR13 to terminal 10 of U4 which is the input to a 14-stage binary counter of the same type as U3. Counter U4 is reset when a positive voltage is applied to reset terminal 11. A reset signal is provided by the capacitor C1 resistor R4 voltage divider when the circuit is powered up. The output of U4 at the 14th stage of the binary counter at pin 3 is connected through diodes CR9 and OR'ed with the end of treatment command signal from treatment timer 60 and the resultant signal is passed through resistor R43 to indicator circuit 70. The signal is also provided, as indicated above, through J5 and resistor R43 and diode CR2 to inhibit generation of pulses when either the selected time from the treatment timer has elapsed or when the stimulator is in the "off" time interval.

The "off" timer is mechanized in FIG. 2B utilizing Schmitt trigger circuit U2B. The feedback resistors include a calibration resistor R7 and the physician controlled resistor 68. Capacitor C4 causes the circuit to oscillate in the same manner as the "on" timer, but at a slower rate to allow for the longer off intervals utilized in the preferred embodiment. The output signal of oscillator U2B at terminal 8 is connected through diode CR12 to the input to counter U4.

Oscillators U2B and U2D do not operate at the same time. The circuitry comprised of diode CR14, diode CR11 and Schmitt trigger U2C operates as a toggle to enable either U2B or U2D to oscillate at any one time. U2C is connected as an inverter. When the stimulation device is in the "on" cycle, pin 3 of U4 is at a low voltage so that the U2D oscillator is operating as the binary counter U4 counts until the output of binary stage 14 at pin 3 switches to a high voltage. When that voltage switches, it shuts down the stimulator by feeding the positive voltage through CR9 and jack J5 in the same way that the end of treatment command from treatment timer 60 is fed. The high voltage at pin 3 of U4 feeds through CR14 to stop the operation of oscillator U2D. That high voltage is also conducted through resistor R44 to U2C which inverts it to remove the high logic signal that was conducted through CR11 to keep oscillator U2B stopped. Thus, U2B starts to operate when U2D is shut down. By adjustment of the operating frequencies of U2D and U2B, the on and off times of the preferred embodiments shown can be adjusted over ranges of 2 to 25 and 2 to 50 seconds, respectively.

The constant stimulation momentary on switch block 56 has a switch designated S3 in FIG. 2A. When switch S3 is actuated, it connects the cathode of CR8 to ground. This inhibits signals coming from jack J5, preventing output circuit to turn off. The treatment timer 60 and the cycle timer 62 are inhibited from shutting the circuit off during the time that the momentary contact switch S3 is closed.

The closure of switch S3 also applies a ground to the input of U2C which puts a high logic signal on the output of U2C to stop oscillator U2B. This operational feature allows oscillator U2D to keep running until U4 reaches the end of its time cycle so that when the pressure on the constant stimulation button S3 is removed, the cycle timer is in the "off" position and at the beginning of the "off" cycle. This is an important operational feature because after continued stimulation under control of the constant stimulation switch has been applied to a muscle group, it is extremely desirable to allow the muscle to recover in a nonstimulated condition. Allowing the "on" cycle timer to continue to run to bring the circuit back into the beginning of the "off" cycle during the time that constant stimulation is applied accomplishes this desirable objective in the preferred embodiment of the stimulator shown.

It should also be noted that actuation of the constant stimulation button S3 does not reset the treatment timer 60.

The output signal at terminal 3 of counter U4 is connected through J5 to the cycler indicator lights 70. The signal passes through resistor R5 to the base of NPN transistor Q1 which has its base connected to ground through resistor R41. The collector of Q1 is connected to the base of Q2 through resistor R12. A green light emitting diode CR15 is connected to the collector of Q1 while a red LED CR16 is connected to the collector of Q2. The anodes of CR15 and CR16 are connected through a current limiting resistor R11 to the unregulated supply voltage +V. The emitters of Q1 and Q2 are tied together and connected to the collector of NPN transistor Q9 which receives an input signal through R42. Either Q1 or Q2 is turned on, depending upon whether the output of U4 is in a high or low condition. Q9 is turned on for each half cycle of the output of rate oscillator 40. The LEDs thus operate to indicate whether the stimulation is "on" or "off". During the "on" cycle or when S3 is pushed for constant stimulation, the red light of CR16 will come on. During the "off" cycle or once the treatment timer shuts the device down, the green light of CR15 comes on. Since Q9 is turned on and off at the rate of the rate oscillator, the light emitting diodes CR15 and CR16 are blinked at a rate corresponding to the rate of the oscillator and the power consumption to drive the indicators is substantially reduced. If the rate of oscillator 40 is set at a very low rate, the blinking is visible to the user's eye.

The signal from the output of timers U3 and U4 after passing through the normally closed contacts 90 of J5 is conducted through resistor R43, CR2, conductor 93 and resistor R16 to the base of NPN transistor Q3. The base of Q3 is connected to ground through R15. The collector of Q3 is connected through R22 to the base of Q8. The emitter of NPN transistor Q8 is connected to the regulated supply +V1. The base of Q8 is connected to the regulated supply +V1 through resistor R45 and the collector of Q8 is connected through R23 to diodes CR26 and CR23 at the inputs of identical channel 1 and channel 2 ramp circuits 48 and 50, respectively, as shown in FIG. 2C. The detailed circuitry of pulse width circuits 32 and 34 are also identical. Accordingly, it is necessary only to describe the operation of the channel 1 output circuitry since the channel 2 output circuitry is essentially identical.

When the U3 or U4 timers switch to a positive signal, that signal charges capacitor C9 of ramp circuit 48 rapidly through resistor R23 which has a low impedance. The positive voltage applied at noninverting input terminal 5 of U1C produces a positive voltage at the output terminal 7 of U1C which is connected through resistor R25 to the noninverting input of U1D in the channel 1 pulse width circuit. Thus, when a positive voltage is applied to CR26, a positive signal is applied at the input of pulse width circuit 32 which, as described below, turns off the channel 1 output. When the positive signal holding channel 1 off is removed from the anode of CR26, capacitor C9, which had been previously charged to a high logic signal, begins to discharge through the series combination of adjustable resistor 52 and fixed resistor R18.

Since U1C is connected as a voltage follower, the positive output of U1C gradually diminishes. The diminishing ramp signal from the output of ramp circuit 48 is summed in the pulse width circuit 32 with a rate signal on conductor 36 produced by rate oscillator 40, the operation of which is discussed below.

The square wave rate signal on conductor 36 is passed through capacitor C10 to the wiper of variable resistor R38 and through resistor R27 to the noninverting input terminal 3 of U1D. A diode CR25 has its anode connected to ground and its cathode connected to pin 3 of U1D. The values of R38, R27 and C10 are selected to give a time constant which, when applied to the square wave signal at the output of oscillator 40, produces a nominal 225 microsecond pulse width for the output pulses. The pulse width of the drive signal on conductor 28 is inversely dependent upon the magnitude of the ramp input to U1D produced by the ramp circuit 48. As the output of U1C follows C9 to zero, +V1 divides across R26 and R25 to ground through U1C to provide a fixed bias to pin 2 of U1D.

The signal on conductor 28 is connected to the output circuit 16 of channel 1. The signal is an increasing pulse width signal beginning from a very narrow signal when the positive voltage is removed from the anode of CR26 and increasing to the full nominal pulse width after the ramp signal at the output of the ramp circuit 48 decreases to zero in accordance with the setting of ramp adjustment control 52. As the output of U1C follows C9 to zero, +V1 divides across R26 and R25 to ground through U1C to provide a fixed bias to pin 2 of U1D. The leading edge of the pulse occurs at intervals determined by the square wave signal produced by oscillator 40 so the leading edges of the drive pulses on conductor 28 occur at a fixed pulse rate.

Rate oscillator 40 is based on Schmitt trigger U2E and its adjustable feedback resistors R13 and 46 and timing capacitor C6. The drive signal to channel 1 is inverted by Schmitt trigger U2F so that the identical drive circuitry of channels 1 and 2 is not in the "on" condition at the same time. This is necessary to avoid undesirable overloading of the power supply. Cells BT1, BT2 and BT3 provide the power for the device. Capacitors C11 and C12 are large capacitors used to facilitate driving the output current. They are back-to-back to prevent damage due to improperly installed batteries.

Because the output circuits 16 and 18 are identical, only the channel 1 output circuit 16 is described in detail. The drive signal on conductor 28 is passed through a variable calibration resistor R28, the physician amplitude control 24 and the drive signal for Q4 is taken from the wiper of the patient adjustment amplitude control 20. The winding of potentiometer or a variable resistor 20 is connected to the base of a grounded emitter open collector NPN transistor Q11 to provide temperature and base-emitter voltage compensation for Q4. The collector of Q4 is connected to the base of PNP Darlington transistor pair Q5 which has its emitter connected to the +V supply. The Darlington base junction is also connected to the positive supply through R33. The collector of Q5 is connected through the primary winding of isolation transformer T1 and a current measuring resistor R31 to ground. R31 has an extremely low resistance and serves as a current sensor to force Q5 to drive a constant current in the primary of T1.

The current feedback is obtained as follows. The base-emitter voltage of Q4 and Q11 are matched so that the voltage from control 20 is applied to R31 to drive a current therein proportional to the setting of 20. Thus, the T1 primary current is fixed at a selected current. T1 acts as a current transformer to produce a constant current output for load impedance from 100 to 1,000 ohms.

A flyback diode CR17 suppresses the inductive surge voltage across the primary winding of transformer T1 when Q5 shuts off at the completion of a pulse.

The secondary winding of transformer T1 is connected to output terminals 12. Zener diode CR19 is a safety diode to prevent the voltage across output terminals 12 rising to an excessive value if the output impedance across terminals 12 is extremely high due to a loose electrode or some similar kind of open circuit condition. Diode CR18 is used to keep CR19 from forward conducting during the negative or biphasic portion of the pulse, thus maintaining a zero net DC output to the patient. The transformer produces a balanced biphasic rectangular waveform with a zero net DC component to minimize the possibility of skin rash developing from stimulation.

The device is operated as follows. Fresh, fully-recharged batteries BT1, BT2 and BT3 are installed. Both amplitude controls 20 and 22 are set with S1 and S2 in the off position and at minimum resistance and the clinician or physician operated amplitude limit controls 24 and 26 are set at initially 50% of appropriate levels. These and other clinician controls are set to produce minimal muscle fatigue while comfortable to the patient. The on and off time controls are also preset. Generally, on off-time of twice the on-time will avoid fatigue and a ramp time of approximately two seconds will produce a good, comfortable contraction. A selected pulse rate of 30–35 pulses per second will produce a fused contraction with minimal fatigue. If the amplitude settings of controls 24 and 26 are insufficient to produce an adequate muscle contraction, then they may be adjusted upward until a good contraction is achieved.

After the clinician controls are initially adjusted, the cables and electrodes are connected at jacks 12 and 14 and the electrodes are attached to the patient. The treatment time switch 64 is set in the continuous position and the constant stimulation button S3 is depressed while the patient amplitude adjustments 20 and 22 are advanced to produce a fused, but comfortable, contraction. If an adequate contraction is not achieved, even when the amplitude knobs are set to their maximum setting, the controls are returned to the minimum setting and the physician amplitude controls 24 and 26 are advanced by another increment before the patient adjusted amplitude controls 20 and 22 are again adjusted. When an adequate contraction is achieved, the constant stimulation S3 is released and the treatment time switch is set for the desired time interval, allowing treatment to begin.

What is claimed is:

1. A muscle stimulator comprising, in combination:
   oscillator means for producing a periodic output signal at a predetermined repetition rate;
   rate control means coupled to said oscillator means for altering the repetition rate of said oscillator means;
   inverter means, coupled to receive the output of said oscillator means, for producing a periodic output signal having a polarity opposite to that of the periodic output signal produced by said oscillator means;
   treatment timer means for generating a first logic signal after a predetermined treatment time interval;
   treatment timer control means coupled to said treatment timer means for establishing the predetermined treatment time of said treatment timer means;
   cycler means for repetitively producing a second logic signal which remains at a first logic level for a predetermined "on" time interval and a second logic level for a predetermined "off" time interval;
   first cycler control means completed to said cycler means for setting the predetermined "on" time interval of said cycler means;
   second cycler control means coupled to said cycler means for setting the predetermined "off" time interval of said cycler means;
   external switch means;
   plug means operatively connected to said external switch means;
   accessory jack means constructed and arranged for receiving said plug means and for providing a third logic signal when said plug means is inserted in said jack means and said external switch means is in a particular condition or when said plug is not inserted in said jack;
   momentary contact switch means for producing a fourth logic signal when said momentary on switch means is actuated;
   first and second ramp generator circuit means connected to receive said first, second, third and fourth logic signals and for producing first and second output ramp signals changing from a first to a second level at first and second predetermined rates, subsequent to receipt of either of said first, second, third or fourth logic signals;
   first and second ramp generator control means coupled respectively to said first and second ramp generator circuit means for independently altering the rate of change of the output ramp signals of said first and second ramp generator circuit means;
   first pulse width circuit means coupled to receive the ramp signal from said first ramp generator circuit means and to receive the periodic output signal from said oscillator means and for producing a fixed amplitude pulse signal having a pulse width increasing at a rate proportional to the rate of change of the ramp signal from said first ramp generator circuit means at the predetermined repetition rate of said oscillator means until the output signal of said second ramp generator circuit means reaches the second level and the pulse width of the pulse signal reaches a predetermined pulse width;
   second pulse width circuit means coupled to receive the ramp signal from said second ramp generator circuit means and to receive the inverted periodic output signal of said inverter means and for producing a fixed amplitude pulse signal having a pulse width increasing at the rate of change of said ramp from said second ramp generator circuit means at the predetermined repetition rate of said oscillator means until the output signal of said second ramp generator circuit means reaches the second level and the pulse width of the pulse signal reaches a predetermined pulse width;
   first and second output circuit means connected to receive the pulse outputs of said first and second pulse width circuit means respectively and for producing a balanced biphasic constant current output signal; and
   first and second output circuit control means for adjusting the current amplitude of the output pulses of said first and second output circuits respectively.

2. The invention of claim 1 wherein said rate control means is constructed and arranged for altering the repetition rate of said oscillator means between 3 and 50 pulses per second.

3. The invention of claim 1 wherein said treatment timer control means is constructed and arranged for establishing the treatment time of said treatment timer means at 15, 30 or 60 minutes or continuous.

4. The invention of claim 1 wherein said first cycler control means is constructed and arranged for setting predetermined "on" time intervals between 2 and 25 seconds.

5. The invention of claim 1 wherein said second cycler control means is constructed and arranged for setting predetermined "off" time intervals between 2 and 50 seconds.

6. The invention of claim 1 wherein said first and second ramp generator control means are constructed and arranged for varying the rate of increase of said first and second output ramp circuits from first to second levels between 0.5 and 8 seconds.

7. The invention of claim 1 wherein said first and second output circuit control means is constructed and arranged for adjusting the amplitude of the output pulses between 30 and 100% of a maximum output current.

8. The invention of claim 7 wherein said first and second output circuit means are constructed and arranged to provide a maximum constant output current between 90 and 100 milliamps over a load impedance range of 100 to 1,000 ohms.

9. A muscle stimulator comprising, in combination:
   oscillator means for producing a periodic output signal at a predetermined repetition rate;
   inverter means, coupled to receive the output of said oscillator means, for producing a periodic output signal having a polarity opposite to that of the periodic output signal produced by said oscillator means;
   treatment timer means for generating a first logic signal after a predetermined treatment time interval;
   cycler means for repetitively producing a second logic signal which remains at a first logic level for a predetermined "on" time interval and a second logic level for a predetermined "off" time interval;
   external switch means;

plug means operatively connected to said external switch means;

accessory jack means constructed and arranged for receiving said plug means and for providing a third logic signal when said plug means is inserted in said jack means and said external switch means is in a particular condition or when no plug is inserted in said jack;

momentary contact switch means for producing a fourth logic signal when said momentary on switch means is actuated;

first and second ramp generator circuit means connected to receive said third and fourth logic signals and for producing first and second output ramp signals changing from a first to a second level at first and second predetermined rates, subsequent to receipt of said first, second, third or fourth logic signals;

first pulse width circuit means coupled to receive the ramp signal from said first ramp generator circuit means and to receive the periodic output signal from said oscillator means and for producing a fixed amplitude pulse signal having a pulse width increasing at a rate proportional to the rate of change of the ramp signal from said first ramp generator circuit means at the predetermined repetition rate of said oscillator means until the output signal of said second ramp generator circuit means reaches the second level and the pulse width of the pulse signal reaches a predetermined pulse width;

second pulse width circuit means coupled to receive the ramp signal from said second ramp generator circuit means and to receive the inverted periodic output signal of said inverter means and for producing a fixed amplitude pulse signal having a pulse width increasing at the rate of change of said ramp from said second ramp generator circuit means at the predetermined repetition rate of said oscillator means until the output signal of said second ramp generator circuit means reaches the second level and the pulse width of the pulse signal reaches a predetermined pulse width; and first and second output circuit means connected to receive the pulse outputs of said first and second pulse width circuit means respectively and for producing an output signal.

10. A muscle stimulator comprising, in combination:

oscillator means for producing a periodic output signal at a predetermined repetition rate;

treatment timer means for generating a first logic signal after a predetermined treatment time interval;

cycler means for repetitively producing a second logic signal which remains at a first logic level for a predetermined "on" time interval and a second logic level for a predetermined "off" time interval;

external switch means;

plug means operatively connected to said external switch means;

accessory jack means constructed and arranged for receiving plug means and for providing a third logic signal when said plug means is inserted in said jack means and said external switch means is in a particular condition or when no plug is inserted in said jack;

momentary contact switch means for producing a fourth logic signal when said momentary on switch means is actuated;

first and second ramp generator circuit means connected to receive said third and fourth logic signals and for producing first and second output ramp signals changing from a first to a second level at first and second predetermined rates, subsequent to receipt of said first, second, third or fourth logic signals;

first pulse width circuit means coupled to receive the ramp signal from said first ramp generator circuit means and to receive the periodic output signal from said oscillator means and for producing a fixed amplitude pulse signal having a pulse width increasing at a rate proportional to the rate of change of the ramp signal from said first ramp generator circuit means at the predetermined repetition rate of said oscillator means until the output signal of said second ramp generator circuit means reaches the signal level and the pulse width of the pulse signal reaches a predetermined pulse width;

second pulse width circuit means coupled to receive the ramp signal from said second ramp generator circuit means and to receive the periodic output signal from said oscillator means and for producing a fixed amplitude pulse signal having a pulse width increasing at the rate of change of said ramp from said second ramp generator circuit means at the predetermined repetition rate of said oscillator means until the output signal of said second ramp generator circuit means reaches the second level and the pulse width of the pulse signal reaches a predetermined pulse width;

first and second output circuit means connected to receive the pulse outputs of said first and second pulse width circuit means respectively and for producing an output signal; and further means operatively coupled to said first and second pulse width circuit means and said oscillator means for causing said first and second pulse width circuit means to produce said first and second output pulse signals alternately at the predetermined repetition rate of said oscillator means.

11. A muscle stimulator comprising, in combination:

oscillator means for producing a periodic output signal at a predetermined repetition rate;

inverter means, coupled to receive the output of said oscillator means, for producing a periodic output signal having a polarity opposite to that of the periodic output signal produced by said oscillator means;

treatment timer means for generating a first logic signal after a predetermined time interval;

cycler means for repetitively producing a second logic signal which remains at a first logic level for a predetermined "on" time interval and a second logic level for a predetermined "off" time interval;

logic means connected to receive said first and second logic signals and provide a third logic signal when either said first or said second logic signals are received;

first and second ramp generator circuit means connected to receive said third logic signal and for producing first and second output ramp signals changing from a first to a second level at first and second predetermined rates, subsequent to receipt of said third logic signal;

first pulse width circuit means coupled to receive the ramp signal from said first ramp generator circuit means and to receive the periodic output signal from said oscillator means and for producing a fixed amplitude pulse signal having a pulse width increasing at a rate proportional to the rate of change of the ramp signal from said first ramp generator circuit means at the predetermined repetition rate of said oscillator means until the output signal of said second ramp generator circuit means reaches the second level and the pulse width of the pulse signal reaches a predetermined pulse width;

second pulse width circuit means coupled to receive the ramp signal from said second ramp generator circuit means and to receive the inverted periodic output signal of said inverter means and for producing a fixed amplitude pulse signal having a pulse width increasing at the rate of change of said ramp from said second ramp generator circuit means at the predetermined repetition rate of said oscillator means until the output signal of said second ramp generator circuit means reaches the second level and the pulse width of the pulse signal reaches a predetermined pulse width; and first and second output circuit means connected to receive the pulse outputs of said first and second pulse width circuit means respectively and for producing an output signal.

12. A muscle stimulator comprising:

output enabling means for producing an enabling signal to enable generation of output pulses by said stimulator;

interval timing means connected to receive the enabling signal from said output enabling means and for generating repetitive bursts of pulse initiating signals, the time duration of each burst of pulse initiating signals being a first predetermined time interval and the time interval separating said bursts of pulse initiating signals being a second predetermined time interval, said interval timing means including means for independently adjusting said first and said second time intervals;

further timing means connected to receive pulse initiating signals from said interval timing means and for producing output signals having fixed pulse amplitude and a pulse width increasing from zero to a selected value over a third predetermined time interval, upon receipt of the first initiating signal in a burst of pulse initiating signals; and an output circuit connected to receive the output signal from said further timing means and for producing output pulses suitable for stimulation of muscle tissue.

* * * * *

UNITED STATES PATENT AND TRADEMARK OFFICE
CERTIFICATE OF CORRECTION

PATENT NO. : 4,392,496
DATED : July 12, 1983
INVENTOR(S) : David J. Stanton

It is certified that error appears in the above-identified patent and that said Letters Patent are hereby corrected as shown below:

Column 1, line 12, the word appearing as "to" should read --on--.

Column 2, line 25, the word appearing as "exitation" should read --excitation--.

Column 9, line 27, the word appearing as "completed" should read --coupled--.

Signed and Sealed this

Fourth Day of October 1983

[SEAL]

Attest:

Attesting Officer

GERALD J. MOSSINGHOFF

Commissioner of Patents and Trademarks